United States Patent [19]
Weiner et al.

[11] Patent Number: 5,869,054
[45] Date of Patent: *Feb. 9, 1999

[54] TREATMENT OF MULTIPLE SCLEROSIS BY ORAL ADMINISTRATION OF AUTOANTIGENS

[75] Inventors: Howard L. Weiner, Brookline; David A. Hafler, Newton, both of Mass.

[73] Assignee: Autoimmune Inc., Lexington, Mass.

[ * ] Notice: The term of this patent shall not extend beyond the expiration date of Pat. No. 5,849,298.

[21] Appl. No.: 454,832

[22] Filed: May 31, 1995

Related U.S. Application Data

[63] Continuation of Ser. No. 279,275, Jul. 22, 1994, which is a continuation of Ser. No. 460,852, filed as PCT/US88/02139, Jun. 24, 1988, abandoned, which is a continuation-in-part of Ser. No. 65,734, Jun. 24, 1987, abandoned.

[51] Int. Cl.$^6$ ..................................................... A61K 39/00
[52] U.S. Cl. ....................... 424/184.1; 424/451; 424/464; 514/2; 514/12; 514/21; 514/903
[58] Field of Search .......................... 424/184.1; 530/326, 530/327, 328, 329, 330, 350, 356, 387.1, 387.3, 387.5, 868; 514/2, 8, 12, 13, 21, 825, 868, 903

[56] References Cited

U.S. PATENT DOCUMENTS

| | | |
|---|---|---|
| 4,804,745 | 2/1989 | Koepff et al. . |
| 5,075,112 | 12/1991 | Lane . |

FOREIGN PATENT DOCUMENTS

| | | |
|---|---|---|
| 0 304 279 A2 | 2/1989 | European Pat. Off. . |
| 0 271 577 B1 | 10/1995 | European Pat. Off. . |
| WO 80/02501 | 11/1980 | WIPO . |
| WO 88/10120 | 12/1988 | WIPO . |
| WO 91/08760 | 6/1991 | WIPO . |
| WO 92/06704 | 4/1992 | WIPO . |
| WO 92/06708 | 4/1992 | WIPO . |
| WO 93/02699 | 2/1993 | WIPO . |
| WO 93/16724 | 9/1993 | WIPO . |
| WO 93/21222 | 10/1993 | WIPO . |

OTHER PUBLICATIONS

▲ Allegretta, M., et al., *Science*, 247:718–721, 1990.
♦ Avrilionis, K. and Boggs, J.M., *J. Neuroimmunol.* 35:210–10, 1991.
▲ Ben–Nun, A., et al., *J. Immunol.*, 129:303–308, 1982.
Bitar et al., *Cell. Immun.*, 122:364–370, 1988.
♦ Burns, F.R., et al., *J. Exp. Med.*, 169:27–39, 1989.
▲ Chen et al., *Science* 265:1237, 1994.
+ Cremer, et al., *J. Immunol.* 87:2995, 1983.
▼ Eisenbarth, G.S., *New Eng. J. Med.* 314:1360–8, 1986.
+ Englert, et al., *Cell. Immunol.* 87:357, 1984.
♦ Gaur et al., *Science* 258:1491–4, 1992.
▼ Harrison et al., *J. Clin. Invest.* 89:1161–5, 1992.
♦ Holoshitz, J. et al, *J. Immunol.* 131:2810, 1983.
▲ Howell, M.D., et al., *Science*, 246:668–670, 1989.
Janeway, *Nature* 341:482–83, 1989.
▲ Khoury, S. J., et al., *J. Exp. Med.* 176:1355, 1992.

+ Lane, I. William et al., *Sharks Don't Get Cancer*, Avery Publishing Group Inc., 1992, updated edition 1993.
▲ Lider et al., *Ann. N. Y. Acad. Sci.*, pp. 267–273, 1986.
♦ Martin, R., et al., *J. Immunol.* 145:540–8, 1990.
▲ Martin, R., et al., *J. of Exper. Med.* 173:19–24, 1991.
▲ Martin, R., et al., *J. Immunol.* 148:1359–1366, 1992.
▲ Miller, A., et al., *J. Exp. Med.* 174:791, 1991.
▲ Miller, A., et al., *Proc. Natl. Acad. Sci. USA* 89:421, 1992.
♦ Miller, A., et al., *J. Immunol.* 151:7307–15, 1993.
♦ Miller, A., et al., *J. Neuroimmunol.* 46:73–82, 1993.
▼ Mori, et al., *Diabetologia* 29:244–7, 1986.
○ Nussenblatt, R. B. et al., *J. Immunol.* 144:1689, 1990.
♦ Ota, K, et al., *Nature*, 346:183–7, 1990.
♦ Pette, M., et al., *Proc. Natl. Acad. Sci., USA* 87:7968–72, 1990.
+ Pinals, R. S., et al., *Arthritis Rheum.* 24:1308, 1981.
+ Rama, et al., *Conncective Tissue Research* 12:111, 1984.
▲ Santos, L. M. B., et al., *J. Immunol.* 150:115A, 1993.
Schwartz, *Ann. Rev. Immunol.* 3:237–61, 1985.
+ Sewel, K.L. and Trentham, D.E., *The Lancet* 341:283, 1993.
+ Steinbrocker, O., et al., *JAMA* 140:659, 1949.
♦ Su, X., et al., *J. Neuroimmunol.* 34:181–190, 1991.
+ Trentham, D. E., et al., *Science* 261:1727, 1993.
♦ Vandenbark, A.A., et al., *Nature*, 341:541–544, 1989.
+ Weinblatt, M.E., et al., *N. Eng. J. Med.* 312:818, 1985.
▲ Weiner et al., (Abstr) *Neurology* (Suppl. 1) 39:172, 1989.
▲ Whitacre, C. C., et al., *J. Immunol.* 147:2155, 1991.
♦ Wucherpfenning, K.W. et al., *Science* 248:1016–9, 1990.
♦ Zamvil, S. S., et al., *Nature* 324:258–260, 1986.
+ Zhang, Z. J., et al., *J. Immunol.* 145:2489, 1990.
▼ Zhang, Z. J., et al., *Proc. Natl. Acad. Sci. USA* 88:10252 1991.
▲ Zhang, Z. J., et al., *FASEB J.* 6(5) A1693, 1992.
+These references are generally related towards the rheumatoid arthritis claims.
▼These references are generally related towards diabetes mellitus claims.
♦These references are particularly relevant to the claims directed towards the use of Myelin Basic Protein fragments.
▲These references are generally related towards the multiple sclerosis claims.
○These reference are generally related towards other, unclaimed, autoimmune diseases.
AutoImmune Press Release of Apr. 21, 1997.
Higgins et al., *J. Immunology*, 140:440–445, 1988.
Eylar, *Adv. Exp. Med. Bio.*, 98:259–281, 1978.
Sriram et al., *Cell. Immunol.*, 75:378–382, 1983.

(List continued on next page.)

*Primary Examiner*—Ponnathapura Achutamurthy
*Attorney, Agent, or Firm*—Darby & Darby

[57] ABSTRACT

The invention is directed to a method of treating a T cell-mediated autoimmune disease in animals, including humans, by the oral or enteral administration of autoantigens, fragments of autoantigens, or analogs structurally related to those autoantigens, which are specific for the particular autoimmune disease. The method of the invention includes both prophylactic and therapeutic measures.

30 Claims, 6 Drawing Sheets

OTHER PUBLICATIONS

Nagler–Anderson et al., *PNAS*, 83:7443–7446, 1986.
Scohoen, *J. Immunol.*, 128:717–719, 1982.
Higgins et al., *Annals Neurology*, abstract No. P154, 1986.
Whitacre et al., *6th Int'l. Cong. Immunol.*, abstract No. 3.62.21, 1986.
Zamvil et al., *Nature*, 324:258–260, 1986.
Fritz et al., *J. Immunol.*, 134:2328–2332, 1985.
Fritz et al., *J. Immunol.*, 130:191–194, 1983.
Pettinelli et al., *J. Immunol.*, 129:1209–1211, 1982.
Whitaker et al., *J. Bio. Chem*, 250:9106–9111, 1975.
Thompson et al., *Clin. Exp. Immunol.*, 64:581–586, 1985.
Lider et al., *J. Immunol.*, 142:748–752, 1989.
Friedman et al., *PNAS* 91:6688–6692, 1994.
Bitar, dissertation entitled, *The Suppressive Effects of Oral Myelin Basic Protein* . . . , 1986.
Nagler–Anderson, dissertation entitled, *Immunoregulation of an Exp. Model of Autoimmunity*, 1986.
Rothbart, *1st Forum in Virology*, pp. 518–520, 1986.
Eylar et al., *Neurochem. Research*, 4:249–258, 1979.
Kagnoff, *Oral Tolerance*, pp. 248–269, 1982.
Mowat, *Immunol. Today*, 8:93–98. 1987.
Weiner et al., *Science*, 259:1321–1324, 1993.
Campbell et al, *Arch. Neurol.*, 29:10–15, 1973.
Carnegie et al., *Immunol.* 19:55–63, 1970.
Fritz et al., *J. Immunol.*, 130:1024–1026, 1983.
Hashim et al., *Arch. Biochem. and Biophy.*, 156:287–297, 1973.

TREATMENT OF MULTIPLE SCLEROSIS BY ORAL ADMINISTRATION OF AUTOANTIGENS

This is a continuation, of application Ser. No. 08/279,275 filed Jul. 22, 1994 which is a continuation of application Ser. No. 07/460,852, filed Feb. 21, 1990 (now abandoned), which is the national stage of PCT/US88/02139, filed Jun. 24, 1988 which is a continuation-in-part of 07/065,734, filed Jun. 24, 1987 (now abandoned).

BACKGROUND OF THE INVENTION

1. Field of the Invention

The present invention relates to the field of treatment of autoimmune diseases and in particular T cell-mediated or T cell-dependent autoimmune diseases. The present invention teaches the oral or enteral administration of autoantigens, or fragments or analogs thereof, to prophylactically and therapeutically treat these auto-immune diseases.

2. Brief Description of the Background Art

Autoimmune diseases are caused by an abnormal immune response involving either cells or antibodies directed against normal tissues. A number of strategies have been developed to suppress autoimmune diseases, most notably drugs which nonspecifically suppress the immune response. A method of inducing immunologic tolerance by the oral administration of an antigen to prevent autoimmune responses was first demonstrated by Wells in 1911. Wells, H., *J. Infect. Dis.* 9:147 (1911). The oral induction of unresponsiveness has also been demonstrated for several T-cell dependent antigens. Ngan, J. et al., *J. Immunol.* 120:861 (1978), Gautam, S. et al., *J. Immunol.* 135:2975 (1985), Titus, R. et al., *Int. Arch. Allergy Appl. Immun.* 65:323 (1981). Furthermore, a recent publication describes the oral administration of collagen to suppress collagen-induced arthritis in a mouse model. Nagler-Anderson et al., *Proc. Natl. Acad. Sci. (USA)* 83:7443–7446 (1986).

Scientists have also studied ways to suppress autoimmune diseases in various animal models. Experimental allergic encephalomyelitis (EAE) is a T cell-mediated autoimmune disease directed against myelin basic protein (MBP) and has been studied as a model for multiple sclerosis in several mammalian species. See, Alvord, E. et al., *Experimental Allergic Encephalomyelitis A Useful Model For Multiple Sclerosis* (Allan R. Liss, New York, 1984). Immunoregulation of EAE is known to be at least partially dependent on suppressor T cells (Ts). It has been shown that Ts are present in rats which have recovered from EAE. Swierkosz, J. et al., *J. Immunol.* 119:1501 (1977). Furthermore, it has been shown that suppressor T cells account for the unresponsiveness to EAE that is exhibited by some mouse strains. Lando, Z. et al., *Nature* 287:551 (1980).

Various methods have been employed to induce antigen-specific suppression of EAE and include immunization with MBP emulsified in incomplete Freund's adjuvant, as shown by Lando, Z. et al., *J. Immunol.* 126:1526 (1981), and intravenous injection of MBP-conjugated lymphoid cells as shown by Sriram, S. et al., *Cell. Immunol.* 75:378 (1983).

Three papers by Alvord et al. are reported in *Annals of Neurology* in Vol. 6 at pp. 461–468, 468–473, and 474–482, respectively (1979). The first and second of these papers disclose the suppression of EAE in monkeys by the parenteral administration of MBP only when administered together with a nonspecific adjunctive factor, e.g., an antibiotic or a steroid. The third report discloses the presence in the cerebrospinal fluid of patients with multiple sclerosis of several proteases that degrade MBP to antigenically active peptide fragments.

Papers by Traugott et al., *J. Neurological Science* 56:65–73 (1982), and Raine et al., *Lab. Investigation* 48:275–84 (1983) disclose that treatment of a strain of guinea pigs suffering from chronic relapsing EAE by parenterally administered MBP alone or in incomplete Freund's adjuvant (IFA) or in combination with a lipid hapten of myelin, namely, galactocerebroside, suppressed the clinical symptoms of EAE.

Furthermore, McKenna et al., *Cell. Immun.* 81:391–402 (1983), discloses that preinjection of rats with guinea pig MBP coupled to syngeneic spleen leukocytes or to syngeneic red blood cells suppressed the subsequent induction of EAE using guinea pig MBP in Freund's complete adjuvant. The degree of suppression correlated positively with the amount of MBP administered.

A report by Strejan et al., *Cell. Immun.* 84:171–184 (1984), discloses that preinjection of rats with guinea pig MBP encapsulated within phosphatidylserine liposomes suppressed the clinical signs and symptoms of EAE that appear in rats injected with guinea pig MBP in complete Freund's adjuvant.

Another paper by McKenna et al., *Cell. Immun.* 88:251–259 (1984), discloses that the suppressive effects of injected guinea pig MBP leukocyte complexes disclosed in their 1983 report was abolished when animals were pretreated with cyclophosphamide, a drug that inhibits the production of suppressor T lymphocytes.

A report by Krasner et al., *Neurology* 36:92–94 (1986) discloses that synthetic C copolymer I, which is being tested as a treatment for multiple sclerosis because it protects animals against EAE, does not exhibit immunologic cross-reactivity with MBP.

Additionally, a report from the Soviet Union, Belik et al., *Vopr. Med. Khim.* 24:372–377 (1978), discloses (according to an English abstract) the parenteral administration of "alkaline myelin protein fragment" and "synthetic encephalitogenic peptide" to guinea pigs with EAE. The animals recovered after administration of "alkaline myelin protein fragment" to said animals sensitized by bovine "alkaline myelin protein fragment" or by "synthetic encephalitogenic peptide."

A report by Braley-Mullen et al., *Cell. Immun.* 51:408 (1980), and the report by Nagler-Anderson et al. noted above, both disclose the suppression of the symptoms of two other experimental autoimmune diseases which are induced by injection of animals with autoantigen-lymphocyte conjugates. The Braley-Mullen et al. report discloses the suppression of experimental autoimmune thyroiditis in the guinea pig by injection of these animals with thyroglobulin antigen in incomplete Freund's adjuvant. The Nagler-Anderson et al. report discloses the suppression of T type II collagen-induced arthritis in the mouse by intragastric administration of soluble, but not denatured, T type II collagens prior to immunization of the animal with T type II collagen in adjuvant.

SUMMARY OF THE INVENTION

The present invention teaches a method of treating a T cell-mediated or T cell-dependent autoimmune disease in an animal comprising the oral or enteral administration to that animal of autoantigens, fragments of autoantigens, or analogs structurally related to auto-antigens specific for the particular autoimmune disease, in an amount effective to treat the autoimmune disease. Both the clinical and histological effects of such diseases are suppressed in a dose-dependent manner. Moreover, the suppression occurs whether the oral or enteral administration occurs before or after onset of the auto-immune disease. Disease is also suppressed by oral or enteral administration of non disease-inducing and disease-inducing fragments of the autoantigen. The oral or enteral administration of autoantigens, therefore, represents an effective, simple method by which an autoimmune disease can be naturally immunoregulated.

DESCRIPTION OF THE PREFERRED EMBODIMENTS

Figure 1:
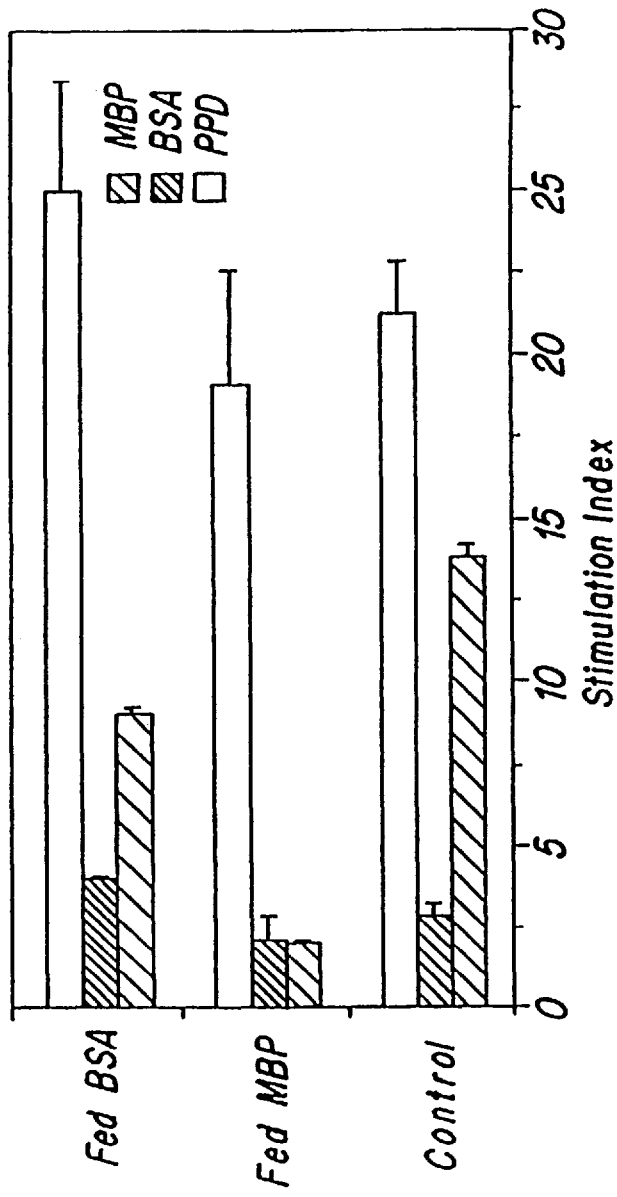
FIG. 1 is a graph which demonstrates the antigen specificity of orally-induced suppression of the proliferative response in Lewis rats. Animals were fed 500 μg of MBP or BSA on days −7, −5 and −2, then immunized with 100 μg MBP in CFA on day 0. Nine days after immunization, lymph nodes were removed and proliferative response to MBP, BSA and PPD (all at 50 μg/ml) determined as described in Example 3. Stimulation index=experimental cpm/control cpm.

The present invention relates to the treatment of T cell-mediated or T cell-dependent autoimmune diseases by the oral or enteral administration of autoantigens specific for such autoimmune diseases as well as biologically active fragments of the autoantigens, and analogs thereof. The term "treatment" is meant to include both the prophylactic measures to prevent such autoimmune diseases as well as the suppression or alleviation of symptoms after the onset of such autoimmune diseases.

An autoimmune disease is a malfunction of the immune system of an animal, including humans, in which the immune system fails to distinguish between foreign substances within the animal and the various substances that the animal itself is composed of. The term "animal" covers all life forms that have an immunoregulatory system and are therefore susceptible to autoimmune diseases.

An "autoantigen" is any substance normally found within an animal that, in an abnormal situation, is no longer recognized as part of the animal itself by the lymphocytes or antibodies of that animal, and is therefore attacked by the immunoregulatory system as though it were a foreign substance. The term "biologically active fragment(s)" of such autoantigens include any partial amino acid sequences thereof that induce the same biological response, i.e., the ability to suppress or eliminate T cell-mediated or T cell-dependent autoimmune response, upon oral or enteral introduction. The term "analog(s)" of such autoantigens include compounds that are so structurally related to these autoantigens that they possess the same biological activity, i.e., the ability to eliminate or suppress T cell-mediated or T cell-dependent autoimmune response, upon oral or enteral introduction. As such, the term includes amino acid sequences which differ from the amino acid sequence of the autoantigen by one or more amino acids (while still retaining substantially equivalent biological activity) as well as chemical compounds which mimic the biological activity of the autoantigens in their ability to suppress or alleviate the symptoms of the disease. Such compounds may consist of tissue from a target organ that is the site of attack in an autoimmune disease.

The primary use of the invention is to treat a large category of diseases that are collectively called autoimmune diseases, including but not limited to multiple sclerosis, myasthenia gravis, rheumatoid arthritis, diabetes mellitus, systemic lupus erythematosus, autoimmune thyroiditis, autoimmune hemolytic anemia, and contact sensitivity disease, which may, for example, be caused by plant matter, such as poison ivy.

Experimental allergic encephalomyelitis (EAE) is a T cell-mediated autoimmune disease directed against myelin basic protein (MBP) and has been studied as a model for multiple sclerosis in several mammalian species. Immunoregulation of EAE is known to be at least partially dependent on suppressor T cells (Ts). It has been shown that Ts are present in rats recovered from EAE and that Ts account for the unresponsiveness to the disease in some mouse strains.

Adjuvant arthritis (AA) is an autoimmune animal model of rheumatoid arthritis which is induced by injecting *Mycobacterium tuberculosis* in the base of the tail of Lewis rats. Between 10 and 15 days following injection, animals develop a severe, progressive arthritis.

The present invention is based on the discovery and confirmation that the oral or enteral administration of MBP is an effective means of suppressing acute monophasic EAE and that the oral or enteral administration of *Mycobacteria tuberculosis* is an effective way of suppressing adjuvant arthritis. Orally or enterally induced tolerance is dose-dependent, and both clinical and histological symptoms of the disease are lessened in severity. Because orally or enterally an irrelevant antigen such as bovine serum albumin (BSA) has no effect on susceptibility to EAE, it can be said that the orally or enterally induced tolerance to EAE is specific for MBP, the antigen to which the T cells that mediate the disease are sensitized.

Furthermore, the oral or enteral administration of MBP to rats induces the suppression of immune responses to MBP. For example, lymphoid cell proliferation and the production of anti-MBP antibodies are both decreased. The cells responsible for both the suppression of the disease and suppression of antigen-specific cellular responses in vitro are of T cell origin and are suppressor/cytotoxic CD8+T lymphocytes.

Thus, as demonstrated below, using the EAE animal model for multiple sclerosis and the animal model for AA, the simple method of administration, orally or enterally, of autoantigens such as MBP, as taught by the invention, is an effective treatment to suppress both the development of autoimmune diseases and certain immune responses to the autoantigens.

By the term "introduction" or "administration" is intended that the autoantigen, its biologically active fragments, or biologically active analogs is introduced into the stomach by way of the mouth through feeding or intragastrically through a stomach tube, i.e., enterally.

In general, the autoantigen, fragment, or analog is introduced, orally or enterally, in an amount of from one to 1000 mg per day, and may be administered in single dose form or multiple dose form. Preferably the autoantigen, fragment, or analog is administered in an amount of from 25 to 850 mg per day. As is understood by one skilled in the art, the exact dosage is a function of the autoantigen, the age, sex, and physical condition of the patient, as well as other concurrent treatments being administered.

Where the autoantigen, fragment, or analog is introduced orally, it may be mixed with other food forms and consumed in solid, semi-solid, suspension, or emulsion form; it may be mixed with pharmaceutically acceptable carriers, flavor enhancers, and the like.

Where the autoantigen, fragment, or analog is administered enterally, it may be introduced in solid, semi-solid, suspension or emulsion form and may be compounded with any of a host of pharmaceutically acceptable carriers, including water, suspending agents, emulsifying agents.

EXPERIMENTAL

Animals: Female Lewis rats weighing 150 to 220 g were obtained from Charles River Laboratory, Wilmington, Mass., and used in all experiments.

Immunization of Animals: Rats were immunized in both hind footpads with 50 $\mu$g guinea pig MBP emulsified in complete Freund's adjuvant (CFA). In some experiments, 50 $\mu$g ovalbumin (OVA) (Sigma) was added to the emulsified antigens and injected similarly. EAE was characterized by limb paralysis and scored as follows: 0) no disease; 1) decreased activity, limp tail; 2) mild paralysis, unsteady gait; 3) moderate paraparesis, limbs splayed apart; and 4) tetraplegia.

Induction of Oral Tolerance: Rats were fed MBP or bovine serum albumin (BSA) five times at three-day intervals 1 mg in 1 ml PBS using a 23-gauge needle covered with plastic tubing.

Proliferation Assay: Nine days after immunization, the rats were sacrificed and their popliteal lymph nodes were removed. A single cell suspension was prepared by pressing the lymph nodes through a stainless steel mesh. A total of $10^5$ lymph node cells (LNC) were cultured with the indicated number of either irradiated (2000 Rads) or intact LNC derived from fed rats in quadruplicate in round-bottomed 96-well plate (Costar). MBP and *Mycobacterium tuberculosis* (Mt), 50 $\mu$g/ml were added to the culture in a volume of 20 $\mu$l. The cultures were incubated for 80 hours and were pulsed with 1 $\mu$Ci [$^3$H] TdR/well for the last 16 hours of culture. The cultures were then harvested on an automatic cell harvester and read on a standard liquid scintillation counter.

Percent suppression of primed LNC (PLNC) proliferation was calculated by the following formula:

$$\% \text{ Suppression} = 100 \times 1 - \frac{CPM \text{ (irradiated } LNC \text{ from fed rat} + PLNC + \text{antigen)}}{CPM \text{ (irradiated } LNC \text{ from untreated rat} + PLNC \text{ antigen)}}$$

Proliferation Media: RPMI (Gibco) was used in all the experiments. The medium was filtered sterile after adding $2\times10^{-5}$M 2-mercaptoethanol, 1% sodium pyruvate, 1% penicillin and streptomycin, 1% non-essential amino acids, and 1% autologous serum.

Purification of Different Cell Subsets: For depletion of CD3, CD4, and CD8 populations from spleen cells, negative selection was used. Petri dishes were coated overnight at 4° C. with 10 ml of 1/1000 goat anti-mouse IgG+IgM antibodies (Tago) in PBS/BSA. The plates were then washed and coated with 3% fetal bovine serum in PBS for 30 min at 20° C. and washed again. Lewis LNC were stained with mouse anti-rat monoclonal antibodies (Serotec/Bioproducts) for CD3 (MRC, OX/38), CD4 (W 3/25), or CD8 (OX/8) diluted 1/100 in PBS. The cells were stained for 30 min on ice, washed, and seeded on the precoated petri dishes, 15 million cells/5 ml PBS/plate, at 4° C. The supernatant containing nonadherent cells was aspirated gently 60 minutes later and centrifuged twice before cell examination and counting. This protocol yields cell populations of about 85–95% purity as examined in the fluorescence activated cell sorter by examining membrane immunofluorescence.

Adoptive Transfer Experiments: Donor rats were fed with either MBP or BSA, 1 mg×5 times, at 3–4 day intervals and sacrificed 4 days after the final feeding. Mesenteric LNC and spleen cells were harvested and injected intraperitoneally either immediately or after activation with concavalin-A (Con-A), 1.5 $\mu$g/ml, in proliferation media for 48 hrs. The number of cells injected for adoptive transfer experiments were as follows: 120×10$^6$ for whole LNC population, either activated or not; 60×10$^6$ for CD3 depleted LNC; 80×10$^6$ for CD4 depleted population; and 95×10$^6$ for CD8 depleted LNC. Recipient Lewis rats were immunized with BP/CFA 4 hrs later for the induction of EAE.

Serum Levels of Antibodies: A solid-phase enzyme-linked immuno-absorbent assay (ELISA) was used for determination of antibody titers against MBP and OVA. Microtiter plates were incubated with 0.1 ml per well of 10 $\mu$g antigen/ml in doubled distilled water. Plates were incubated for 18 hrs at 25° C. After 3 washes with PBS/tween-20 (Bio-Rad), pH 7.5, plates were incubated with 3% BSA/PBS for 2 hrs at 37° C., washed twice, and 100 $\mu$l of diluted serum was added in quadruplicate. The plates were incubated for 2 hrs at 37° C. After three rinses with PBS/tween-20, plates were incubated with 100 $\mu$l/well of peroxidase-conjugated goat anti-rat IgG antibody (Tago, USA) diluted 1:1000 in 1% BSA/PBS for 1 hr at 25° C. Color reaction was obtained by exposure to D-phenylenediamine (0.4 mg/ml phosphate) citrate buffer, pH 5.0) containing 30% $H_2O_2$. The reaction was stopped by adding 0.4N $H_2SO_4$ and OD 492 nm was read on an ELISA reader.

In Vitro Measurement of Antibody Production: Popliteal and splenic LNC were obtained from fed, naive and challenged rats and seeded at a concentration of $10^7$ cells per ml petri dish either alone or irradiated (2000 Rads) together with other PLNC as indicated. The cultures were maintained in proliferation media, with or without antigen (20 $\mu$g/ml), for 3 days in an incubator and then harvested. The diluted supernatants were used to examine the in vitro production and secretion of IgG antibody and were measured for antibody production using an ELISA test as described previously.

Identification of Different Regions of the Myelin Basic Protein Molecule Responsible for Suppression of EAE: Overlapping fragments of the 1–37 region of guinea pig myelin base protein were synthesized using solid phase peptide technique. Houghten, R., Proc. Natl. Acad. Sci. USA 82:5131–5135 (1985). These fragments were then administered orally in equimolar concentrations to 15 mg of whole myelin basic protein. They were administered on day −7, −5, and −2 prior to immunization. Animals were then challenged with basic protein in Freund's adjuvant according to established procedures and scored.

Demonstration that Oral Route of Administration of a Protein Antigen Determines to Which Fragment There Is an Immune Response: Animals were given whole myelin basic protein, either immunized in the foot pad with Freund's adjuvant or administered orally. Seven to 10 days thereafter, spleen and lymph node cells were removed and restimulated in vitro with different fragments of the myelin basic protein molecule.

EXAMPLES

Example 1

The effect of feeding MBP and its peptic fragments on the susceptibility to and severity of acute monophasic EAE was studied in the Lewis rat. Results show that this natural route of tolerance induction suppresses both the development of disease and immune responses to MBP.

To orally induce suppression of EAE, Lewis rats were fed MBP purified from guinea pig brain (Diebler, G., et al., *Prep. Biochem.* 2:139 (1972)) using a syringe equipped with a 20G ball point needle. Control animals were fed equal amounts of bovine serum albumin (BSA) or saline alone. EAE was induced by immunization with 50 ug MBP emulsified in complete Freund's adjuvant (CFA) containing 200 ug *Mycobacterium tuberculosis* by injection into the hind footpads. Disease was characterized by hind limb paralysis and incontinence usually between days 12 and 15 after immunization and in all cases rats recovered by day 16. The first series of experiments investigated the effect of number of feedings and dose of MBP on disease expression. Rats were fed various amounts of MBP either once 7 days before (day −7) the day of immunization (day 0) or three times on days −14, −7 and 0. The results (Table I) demonstrate that feeding MBP to rats suppresses EAE and that orally-induced suppression is dose-dependent. Multiple 500 ug feedings resulted in complete suppression of disease and were more effective than a single feeding at this dose. In addition to clinical manifestation of EAE, histological evidence of disease in rats was examined. Sixteen days after immunization, rats were sacrificed and brains removed and fixed in formalin solution. Fixative was a solution of 100 ml 70% ethanol, 10 ml 37% formalin and 5 ml glacial acetic acid. Slides of paraffin-embedded tissue were prepared from each rat and stained with hematoxylin and eosin. Perivascular inflammatory foci were quantified on coded slides by established procedures (Sobel, R., et al., *J. Immunol.* 132:2393 (1984)). As shown in Table I, feeding rats 500 ug MBP on days −14, −7 and 0 caused a marked decrease in the number of inflammatory lesions in the brain. A moderate decrease was found in animals fed 100 ug and no significant reduction of inflammation was found in rats fed 25 ug MBP.

Example 2

A second series of experiments investigated the effect of feeding MBP prior to or subsequent to immunization with MBP to determine whether the effectiveness of orally-induced suppression is affected by prior exposure to antigen. For these experiments, animals were fed 500 ug MBP three times either before or after active induction of disease (immunization with MBP). The results (Table II) demonstrate that the clinical expression of disease is suppressed whether animals were fed MBP before or after sensitization, the effect being more complete when antigen was fed prior to immunization. However, histologic examination revealed a dramatic reduction of perivascular infiltrates in rats fed MBP either before or after sensitization to MBP. Greater than 60% suppression of disease also occurred when rats were fed three times beginning on days +5 or +7 after immunization (data not shown).

In addition, experiments were performed in which rats were fed 100 ug of MBP at various times, before and after immunization, with MBP. As shown in Table III, disease suppression is seen with single feedings before or after immunization.

Example 3

The effects of oral administration of MBP on cellular and humoral immune responses to MBP were also examined. Proliferative responses to MBP were studied after feeding rats different doses of MBP and following feeding at different times with respect to immunization. Ten days after immunization, rats were sacrificed and single cell suspensions of draining (popliteal) lymph nodes prepared. Cells were cultured in microwells for 4 days, the final 24 hours with $^3$H-thymidine added. A volume of 0.2 ml containing $4\times10^5$ cells in RPMI 1640 containing 2% glutamine, 1% penicillin/streptomycin, $5\times10^{-5}$M 2-mercapto-ethanol and 5% fetal calf serum was added to each microwell and MBP added at 50 ug/ml. Wells were pulsed with 1 $\mu$Ci tritiated thymidine, harvested onto fiberglass filters using a multi-harvester and counted using standard liquid scintillation techniques.

Results (Tables I and II) demonstrate that feeding MBP causes a pronounced (75–92%) decrease in proliferative responses to MBP. Suppression of proliferation, unlike suppression of disease, occurred at all doses and feeding regimens tested, including feeding after immunization. Orally-induced suppression of the proliferative response to MBP is antigen-specific, as shown in FIG. 1. Specifically, feeding MBP does not suppress the proliferative response to purified protein derivative (PPD), an antigen derived from *M. tuberculosis* that induces a proliferative response as a consequence of immunization with CFA. Feeding an irrelevant antigen, BSA, does not affect the proliferative response to PPD and only slightly suppresses the proliferative response to MBP.

Example 4

The effect of feeding MBP on the production of antibody to MBP was also examined. Rats fed MBP were immunized and blood removed by cardiac puncture 16 days following immunization. Levels of anti-MBP antibody in the serum were measured by ELISA. A volume of 0.1 ml of MBP solution (0.05 mg/ml in PBS) was added per microwell and incubated for 3 h at 37° C. Wells were washed with PBS containing 0.05% Tween (PBST) and blocked overnight at 4° C. with 5% BSA in PBS, pH 9.0. After washing wells with PBST, diluted rat sera were added and incubated for 3 h at r.t. and after washing with PBST secondary antibody (peroxidase conjugated goat anti-rat) added for 1 h at r.t. Substrate was added and the reaction was stopped with 0.1 molar NaFl. Plates were read at 450 nm on a Titertek multiscan. Abs$_{450}$ was also determined for serum from rats immunized only with CFA and was subtracted from all values as background.

Unlike suppression of proliferative responses which occurred at virtually all doses and feeding regimens tested, suppression of antibody production was only observed when the animals were fed the highest dose tested (500 $\mu$g) on days −14, −7, and 0 (66% suppression, Table I). Of note is the lack of suppression in rats fed 500 $\mu$g MBP on days −7, −5 and −2 (Table II), suggesting that the temporal sequence in which an identical dose of MBP is fed is important in suppression of antibody responses.

TABLE I

Effect of Feeding Dose on Orally-Induced
Suppression of EAE in Lewis Rats

|  | Induction of EAE | | Immune Response to MBP (percent inhibition) | |
|---|---|---|---|---|
|  | [a]Clinical Disease | [b]Histologic Score | [c]Proliferation | [d]Antibody |
| Immunized Controls Fed day −7 | 19/22 | 9.2 ± 5.8 | — | — |
| 25 μg | 3/5 | ND | 75.6 ± 2 | ND |
| 100 μg | 2/5[e]* | ND | 88.9 | ND |
| 500 μg | 3/10*** | ND | 88.9 ± 2 | ND |
| Fed days −14, −7, 0 | | | | |
| 25 μg | 3/5 | 7.2 ± 5.2 | 82.1 | −48 ± 72 |
| 100 μg | 2/5* | 3.2 ± 1.9 | 80.8 ± 5 | 14 ± 49 |
| 500 μg | 0/10*** | 0.2 ± 0.4 | 87.2 ± 1 | 66 ± 39 |

[a]Rats were fed various doses of MBP on the indicated days and immunized with 50 μg MBP in CFA (200 ug *M. tuberculosis*) on day 0. Shown are the number of diseased rats of the total number immunized. Immunized controls were fed BSA or saline.
[b]Rats were sacrificed on day 16 after immunization and brains removed and fixed. Shown are the average number of perivascular inflammatory foci per animal +/− s.d. ND = not determined.
[c]Proliferative response to MBP was measured for draining lymph node cells ten days after rats were immunized. A volume of 0.2 ml containing $4 \times 10^5$ cells in RPMI 1640 containing 2% glutamine, 1% penicillin/streptomycin, $5 \times 10^{-5}$M 2-mercapto-ethanol and 5% fetal calf serum was added to each microwell and MBP added at 50 μg/ml. Wells were pulsed with 1 μCi tritiated thymidine, harvested onto fiberglass filters using a multiharvester and counted using standard liquid scintillation techniques. Shown is the percentage inhibition of proliferative response to MBP with respect to the immunized control group. Average stimulation index of the immunized controls (MBP-stimulated CPM/background CPM) was 6.0 (29,888 CPM/4960 CPM).
[d]Rats were sacrificed on day 16 and blood drawn by cardiac puncture. Sera were diluted 1/15,625 in PBS and anti-MBP antibody levels were determined by ELISA. A volume of 0.1 ml of MBP solution (0.05 mg/ml in PBS) was added per microwell and incubated for 3 h at 37° C. Wells were washed with PBS containing 0.05% Tween (PBST) and blocked overnight at 4° C. with 5% BSA in PBS, pH 9.0. After washing wells with PBST, diluted rat sera were added and incubated for 3 h at room temperature and after washing with PBST secondary antibody (peroxidase conjugated goat anti-rat) added for 1 h at room temperature. Substrate was added and the reaction was stopped with 0.1M NaFl. Plates were read at 450 nm on a Titertek multiscan. $Abs_{450}$ was also determined for serum from rats immunized only with CFA and was subtracted from all values as background. Shown is the percentage decrease in antibody level, as measured by absorbance of peroxidase substrate at 450 nm, with respect to immunized controls (Mean absorption at $A_{450}$ of immunized controls with background subtracted was 0.148).
[e]Groups were compared by chi-square analysis with one degree of freedom: *p < .05, p < 0.1, *p < .001.

TABLE II

Effect of Feeding MBP to Rats Before or After
Immunization on the Development of EAE

|  | Induction of EAE | | Immune Response to MBP (percent inhibition) | |
|---|---|---|---|---|
|  | [a]Clinical Disease | [b]Histologic Score | [c]Proliferation | [d]Antibody |
| Imunized Controls Days fed 500 μg MBP | 23/26 | 21.6 ± 5.1 | — | — |
| −7, −5, −2, +2, +5, +7 | 0/5[e]*** | 0.2 ± 0.4 | ND | 34 |
| −7, −5, −2 | 0/17*** | 0 | 92.6 | 15 |
| +2, +5, +7 | 4/10** | 1.4 ± 2.3 | 91.5 ± 3 | 15 |

[a]Rats were fed 500 μg MBP on the indicated days and immunized with 50 μg MBP in CFA on day 0. Immunized controls were fed BSA or saline.
[b]See Table I.

TABLE II-continued

Effect of Feeding MBP to Rats Before or After
Immunization on the Development of EAE

|  | Induction of EAE | | Immune Response to MBP (percent inhibition) | |
|---|---|---|---|---|
|  | [a]Clinical Disease | [b]Histologic Score | [c]Proliferation | [d]Antibody |
| Imunized Controls | 23/26 | 21.6 ± 5.1 | — | — |

[c]See Table I. Average stimulation index of immunized controls was 9.4 (82,247 CPM/8,718 CPM).
[d]See Table I. Mean absorption at $A_{450}$ of immunized controls with background subtracted was 0.403.
[e]See Table I.

TABLE III

Orally Induced Suppression of EAE in Lewis Rats

| Feeding Schedule | # Rats Sick/Total |
|---|---|
| None | 11/16 |
| −14, −7, 0, +7 | 0/13 |
| −14 | 1/5 |
| −7 | 0/5 |
| 0 | 1/5 |
| +7 | 1/5 |

Rats were fed 100 μg MBP on the indicated days (with respect to day of immunization = 0), and immunized with 50 μg MBP with CFA (.5 mg/ml *M. tuberculosis*).

Example 5

Further experiments were conducted to determine the persistence of orally-induced protection against EAE. After feeding on days −7, −5 and −2 with 500 ug MBP rats were immunized at various lengths of time after the last feeding. EAE was completely suppressed in rats for up to four weeks after feeding, and by eight weeks 50% of rats fed MBP were again susceptible to disease. The results are shown in Table IV, which indicates that tolerance to the disease is maintained for at least four weeks after the last feeding, with susceptibility to disease induction becoming apparent at eight weeks following feeding.

TABLE IV

Persistence of Orally Induced Tolerance of Lewis Rats

|  |  | # Rats Sick/Total |
|---|---|---|
| Control Fed |  | 9/14 |
| Immunized | day 0 | 0/4 |
|  | day +7 | 0/4 |
|  | day +14 | 0/4 |
|  | day +28 | 0/3 |
|  | day +56 | 4/8 |

Rats were fed 500 μg MBP on days −7, −5, and −2 and immunized on the indicated days with 50 μg MBP in CFA. Control rats (fed BSA) were likewise immunized.

Example 6

It is known that the encephalitogenic region of guinea pig MBP in rats is a specific decapeptide sequence located at residues 75–84, which by itself can induce EAE, whereas other regions of the molecule are non-encephalitogenic (Hashim, G., *Myelin: Chemistry and Biology,* Alan R. Liss, N.Y. (1980)). Furthermore, for other antigens, it has been reported that distinct suppressor determinants exist at sites different from immunogenic determinants (Yowell, R., et al., Nature 279:70 (1979)). It was therefore investigated whether both encephalitogenic and non-encephalitogenic fragments of MBP could prevent EAE via oral administration. Fragments of guinea pig MBP were generated by limited pepsin digestion and separated by column chromatography (Whitaker, J., et al., J. Biol. Chem. 250:9106: (1975)). The three different fragments were fed to rats, then animals were immunized with whole MBP. It was found that both the disease-inducing (fragment 44–89) and non-encephalitogenic (fragments 1–37 and 90–170) peptides suppressed EAE when fed to rats, the non-encephalitogenic fragments being more effective in suppressing the disease than the encephalitogenic fragment (Table V). A decapeptide (S79) was synthesized which differs from the encephalitogenic sequence (residues 75–84) by a single amino acid substitution and is reported to induce suppression when injected into rats with CFA (Kardys, E., et al., J. Immunol. 127:862 (1981)). When S79 (Ala-Gln-Gly-His-Arg-Pro-Gln-Asp-Glu-Gly) was fed to animals it was also found to suppress EAE (Table V). Bovine MBP, which differs from guinea pig MBP at several sites including the encephalitogenic sequence and is not encephalitogenic in rats at doses encephalitogenic for guinea pig MBP (Holoshitz, J., et al., J. Immunol. 131:2810 (1983)), also suppressed disease when fed to animals prior to immunization.

TABLE V

The Effect of Feeding Encephalitogenic and
Non-Encephalitogenic Fragments on the Development
of EAE in Lewis Rats

|  | Clinical Incidence of EAE |
|---|---|
| Immunized Controls | 19/25 |
| MBP fragment 1–37 (109 µg) | 0/9[a]*** |
| MBP fragment 44–89 (135 µg) | 3/11** |
| MBP fragment 90–170 (235 µg) | 0/4** |
| Peptide S79 (30 µg) | 1/8*** |
| Bovine MBP (500 µg) | 0/10*** |

Lewis rats were fed the indicated amounts of MBP fragments or peptides (equimolar to 500 µg whole guinea pig MBP) on days −7, −5 and −2 and immunized on day 0 with 50 µg guinea pig MBP with CFA. Shown are the number of diseased rats of the total number immunized. [a]Groups were compared to immunized controls by chi-square analysis: $p < .01$, *$p < .001$.

EXAMPLE 7

Suppression of Adjuvant Induced Arthritis by Feeding Mycobacteria

Figure 2:
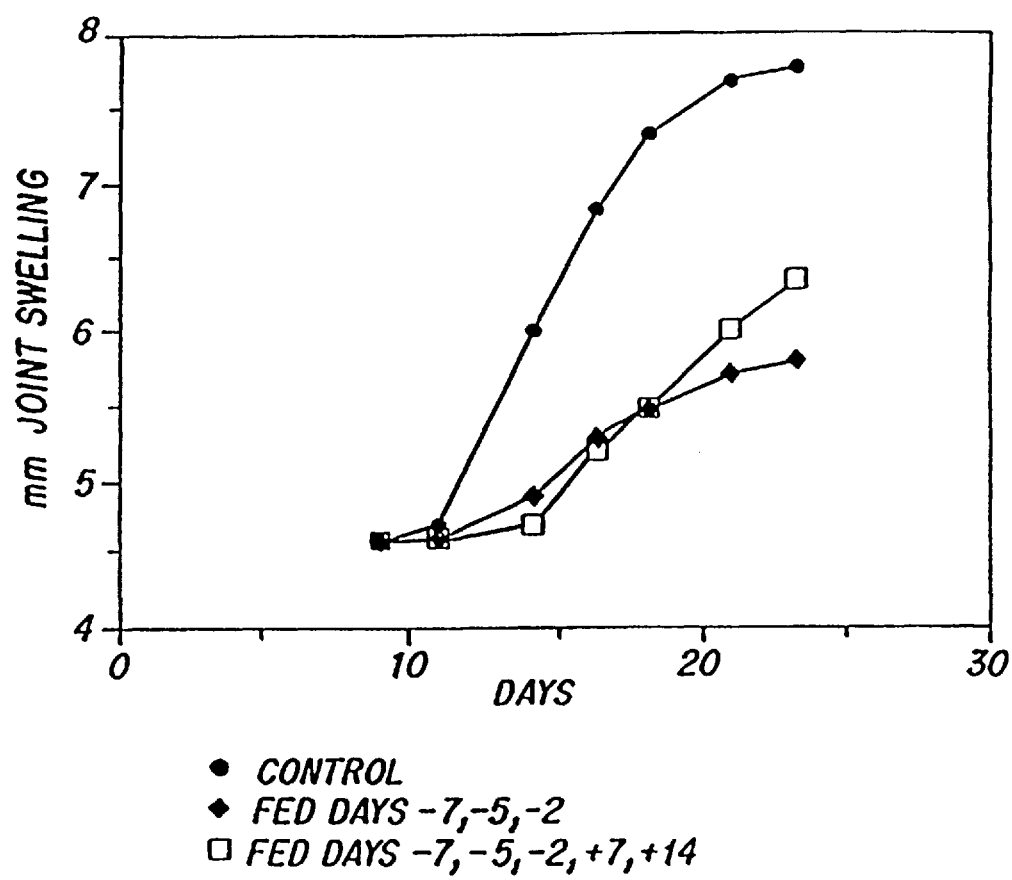
FIG. 2 is a graph which demonstrates orally induced suppression of adjuvant arthritis, as measured by joint swelling.

Adjuvant arthritis was induced in female Lewis rats by immunization with 0.1 ml of 10 mg/ml of complete Freund's adjuvant in the base of the tail. Animals were fed 2.0 mg of Mycobacteria tuberculosis in phosphate buffered saline on days −7, −5, and −2 prior to immunization on day 0 and subsequent to immunization on days +7 and +14. Arthritis was quantitated by measuring joint swelling for three weeks following immunization (Table VI and FIG. 2).

TABLE VI

|  | Joint swelling (mm) on day 21 |
|---|---|
| Control | 7.61 ± 1.4 |
| Days Fed Mycobacteria |  |
| −7, −5, −2 | 5.61 ± 1.1* |
| −7, −5, −2, +7, +14 | 6.07 ± 0.9* |

Joint swelling = thickness of joint on day measured
*$p < 0.01$ compared to control (representative experiment of 4 animals/group)

Example 8

An Adoptive Transfer Model of EAE in the SJL Mouse

Figure 3:
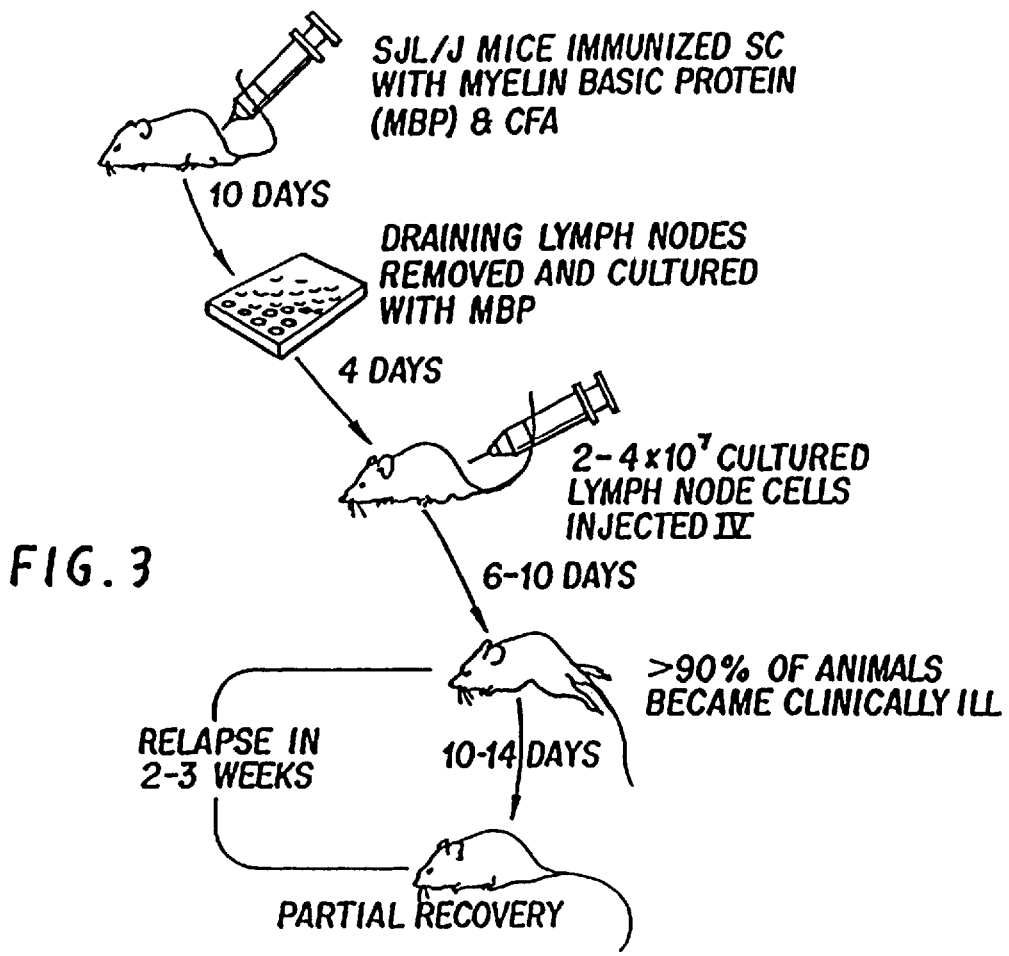
FIG. 3 is a diagrammatic representation of the protocol for inducing relapsing murine EAE.

A workable, reproducible model of adoptive relapsing EAE was established in the SJL mouse. The protocol for this model was adopted from Mokhtarian, et al., Nature, 309:356 (1984). This protocol is depicted graphically in FIG. 3. Briefly, donor animals are immunized with an emulsion containing 400 ug of MBP and 30 ug of M. tuberculosis in CFA. Ten days thereafter, draining lymph nodes are removed and cultured with 50 ug/ml of MBP for four days, washed extensively, and $4-6 \times 10^7$ viable cells are injected intravenously into female recipient animals. Animals are scored for clinical EAE using standard scales, and scored pathologically using standard H & E histological analysis (Brown, A., et al., Lab Invest. 45:278 (1981), Lublin, F., et al., J. Immunol. 126:819 (1981), and Bernard, C. et al., Eur. J. Immunol. 16:655 (1976)). Animals are monitored for at least 100 days after transfer so that the number of relapses can be determined.

Example 9

Orally Induced Suppression of Proliferative Responses in SLJ Mice

Figure 4:
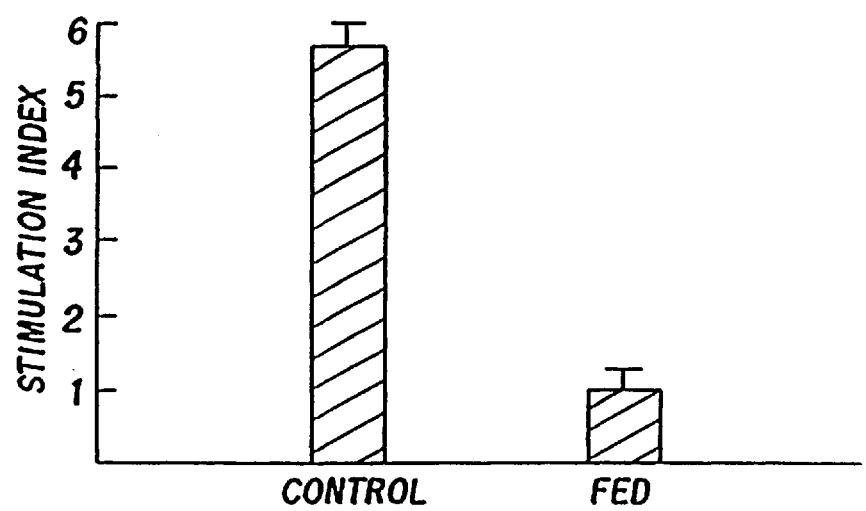
FIG. 4 is a bar graph representing the orally-induced suppression of lymphoid cell proliferation in SJL mice. Animals were fed 400 ug MBP 7 times over a 2 week period and immunized with 400 ug MBP in CFA (0.6 mg/ml *M. tuberculosis*). Stimulation index is MBP-induced proliferation divided by background.

The feeding of 400 ug MBP every other day for two weeks (total of seven separate feedings) prior to immunization with 400 ug MBP in CFA (0.6 mg/ml M. tuberculosis) suppresses the proliferation of lymph node cells in response to MBP immunization. The results are shown in FIG. 4. This Figure depicts the control results versus the feeding results as a function of the MBP-induced proliferation divided by background (Stimulation Index).

The invention is not limited to those modes and embodiments of this application and embodiments that have been described above. It encompasses any modifications that result in the suppression of autoimmune diseases as taught by the present invention. These equivalents are included within the field of protection defined by the claims.

Example 10

Adoptive Transfer of Protective Resistance to EAE Development from MBP Fed Donor Rats to Naive Syngeneic Recipient Rats Donor rats were fed with either MBP or BSA, 1 mg×5 times, at 3–4 day intervals and sacrificed 4 days after the final feeding. Mesenteric lymph node cells (LNC) and spleen cells were harvested and injected intraperitoneally either immediately or after activation with concanavalin-A (Con-A), 1.5 µg/ml, in proliferation media for 48 hrs. The number of cells injected for adoptive transfer experiments were as follows: $120 \times 10^6$ for whole LNC population, either activated or not; $60 \times 10^6$ for CD3 depleted LNC; $80 \times 10^6$ for CD4 depleted population; and $95 \times 10^6$ for CD8 depleted LNC. Recipient Lewis rats were immunized with MBP/CFA 4 hrs later for the induction of EAE. The ability to transfer resistance to development of EAE from fed donor rats to naive syngeneic recipient rats is shown in Table VII. LNC obtained from unfed rats or from bovine serum albumin (BSA) fed donor rats failed to transfer protection against EAE. However, both spleen cells or mesenteric (MES) lymph node cells obtained from MBP fed donors were capable of transferring relative protection against EAE induced in the recipients, demonstrating 50% and 57% suppression of disease, respectively. The mean maximal severity of disease was also reduced markedly in recipients of either spleen cells or mesenteric lymph nodes cells obtained from MBP fed donor rats. These results demonstrate that the oral tolerance to EAE induction is of cellular origin and that the cells responsible for protection are found to be concentrated in both the mesenteric lymph nodes and the spleen.

TABLE VII

Adoptive transfer of protection against EAE using LNC obtained from either fed or untreated donor rats.

| Rats Fed with | Donors Source of LNC | EAE in Recipients Incidence | Mean Max. severity |
|---|---|---|---|
| None | SPC | 6/7 | 2.5 ± 0.3 |
|  | Mes.LNC | 5/5 | 2.6 ± 0.4 |
| BSA | SPC | 4/4 | 2.4 ± 0.2 |
|  | Mes.LNC | 5/5 | 2.6 ± 0.3 |
| MBP | SPC | 4/8* | 1.6 ± 0.2* |
|  | Mes.LNC | 4/7* | 1.7 ± 0.2* |

Lewis rats were fed with either MBP or BSA five times, 1 mg per feeding at 3 day intervals, or remained untreated. The rats were then sacrificed and their spleens and mesenteric lymph nodes were removed. The LNC were harvested and activated for 48 hours in the presence of Con-A. The lymphoblasts were collected, washed three times, and injected intraperitoneally into naive syngeneic rats. The recipient rats were challenged 4 hours later with MBP/CFA for the induction of EAE. The disease was scored daily from day 10 (*Results are statistically significant, $p < 0.05$).

Example 11

Identification of the Lymph Node Cell Subpopulation which mediates Resistance to EAE Con-A activated spleen cells (SPC) obtained from MBP fed donor rats were transferred to naive syngeneic rats either before or after depleting either T cells, helper T lymphocytes (CD4) or suppressor/cytotoxic T lymphocytes (CD8). For depletion of CD3, CD4 and CD8 populations from spleen cells, negative selection was used. Petri dishes were coated overnight at 4° C. with 10 ml of 1/1000 goat anti-mouse IgG+IgM antibodies (Tago) in PBS/BSA. The plates were then washed and coated with 3% fetal bovine serum in PBS for 30 min at 20° C. and washed again. Lewis LNC were stained with mouse anti-rat mono-clonal antibodies (Serotec/Bioproducts) for CD3 (MRC, OX/38), CD4 (W3/25) or CD8 (OX/8) diluted 1/100 in PBS. The cells were stained for 30 min on ice, washed and seeded on the precoated petri dishes, 15 million cells/5 ml PBS/plate, at 4° C. The supernatant containing nonadherent cells was aspirated gently 60 minutes later and centrifuged twice before cell examination and counting. This protocol yields cell populations of about 85–95% purity as examined in the fluorescence activated cell sorter by examining membrane immunofluorescence. The results are demonstrated in Table VIII. The results demonstrate that SPC are capable of transferring protection against EAE (50% incidence), whereas T cell depleted SPC lost their ability to protect recipient rats (group 2). Thus, it seems that the spleen cells which are capable of transferring protection are T lymphocytes. However, depletion of CD8 cells (group 4) results in failure of transferring protection, whereas CD4+depleted SPC showed a significant ability of protecting rats against EAE. Thus, it is evidence that the antigen specific T lymphocytes which are generated after oral administration of MBP and which are mediating resistance to disease induction are of the suppressor/ cytotoxic subset.

TABLE VIII

Adoptive transfer of protection against EAE using depleted population of SPC.

| Group | SPC removed from MBP fed donors | EAE in recipient rats Incidence | Mean Max. Severity |
|---|---|---|---|
| 1 | Whole population | 2/4 | 1.7 ± 0.2* |
| 2 | CD3 depleted | 6/6 | 2.6 ± 0.4* |
| 3 | CD4 depleted | 2/6* | 1.2 ± 0.2* |
| 4 | CD8 depleted | 6/7 | 2.2 ± 0.3 |

Donor rats were fed with MBP, and treated as indicated in the legend of Table 1. The Con-A activated SPC were injected into naive recipient rats either before (group 1) or after depletion of certain subpopulation (groups 2–4). Depletion of CD3, CD4 or CD8 lymhocytes was done by coupling monoclonal IgG antibodies to the SPC and panning. Recipient rats were immunized with MBP/CFA and EAE was recorded from day 10 (*Results are statistically significant, $p < 0.05$).

Example 12

In vitro Suppression of Anti-MBP T Cell Responses by Addition of Lymph Node Cells from MBP Fed Rats Rats were immunized with MBP/CFA and their primed popliteal draining lymph nodes (PLNC) harvested nine days later. A single cell suspension was prepared by pressing the lymph nodes through a stainless steel mesh. A total of $10^5$ LNC were cultured with the indicated number of either irradiated (2000 Rads) or intact LNC derived from fed rats in quadriplicate in round bottomed 96-well plate (Costar). MBP and *Mycobacterium tuberculosis*, 50 µg/ml were added to the culture in a volume of 20 µl. The cultures were incubated for 80 hrs. and were pulsed with 1 µCi [$^3$H] TdR/well for the last 16 hours of culture. The cultures were harvested on an automatic cell harvester and read on a standard liquid scintillation counter.

Percent suppression of primed LNC (PLNC) proliferation was calculated by the following formula:

$$\% \text{ Suppression} = 100 \times 1 - \frac{CPM \text{ (irradiated } LNC \text{ from fed rat} + PLNC + \text{antigen)}}{CPM \text{ (irradiated } LNC \text{ from untreated rat} + PLNC \text{ antigen)}}$$

Figure 5:
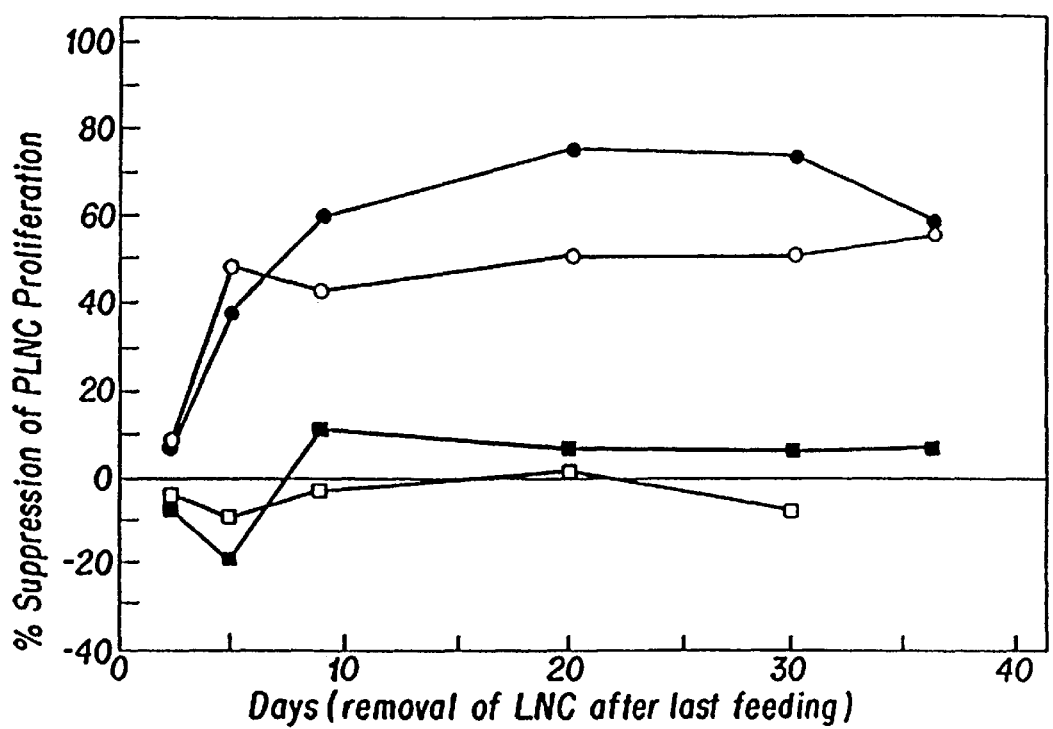
FIG. 5 is a graph which demonstrates the antigen specific suppression of popliteal draining lymph node cells (PLNC) responses by spleen and mesenteric lymph node cells (LNC) obtained from myelin basic protein (MBP) fed rats. The results are expressed as percent suppression of PLNC to MBP (circles) as to *Mycobacterium tuberculosis* (squares). Closed circles or closed squares represent the response of spleen cells. Open circles or open squares represent the response of mesenteric lymph node cells.

The PLNC were cultured along with irradiated SPC or mesenteric LNC obtained from either naive or MBP fed rats in the presence of either MBP or *Mycobacterium tuberculosis*. The LNC obtained from MBP fed donor rats were examined on a different days after last feeding. Results are shown in FIG. 5. It is shown that within the time frame of the experiment, LNC obtained from fed rats did not affect the PLNC responses to *Mycobacterium tuberculosis*. However, both SPC and mesenteric LNC obtained from fed rats were able to suppress the PLNC proliferation to MBP. Antigen specific suppression of PLNC responses was greater using SPC than mesenteric LNC. Suppression is evident from day 5 to day 36 after the last feeding with MBP indicating that the induction of suppression is achieved soon after feeding and it is maintained for a relatively long period of time.

Thus, it seems that LNC obtained from rats rendered to be tolerized to EAE induction are antigen-specific lymphocytes which are capable of suppressing cellular immune responses only to the antigen used for feeding.

Example 13

Suppression of Anti-MBP Responses of PLNC in the Presence of Irradiated SPC and its Subpopulation, Obtained from a MBP Fed Rat To examine the subpopulation of SPC responsible for suppression, SPC were obtained from MBP fed rat 20 days after the last feeding, depleted of certain lymphocyte populations, irradiated and mixed with PLNC obtained from MBP/CFA immunized rat together with MBP. Popliteal and splenic LNC were seeded at a concentration of $10^7$ cells per ml petri dish either alone or irradiated (2000 Rads) together with other PLNC as indicated. The cultures were maintained in proliferation media, with or without antigen (20 μg/nl), for 3 days in an incubator and then harvested. The diluted supernatants were used to examine the in vitro production and secretion of IgG antibody and were measured for antibody production using an ELISA test. Microtiter plates were incubated with 0.1 ml per well of 10 μg antigen/ml in doubled distilled water. Plates were incubated for 18 hrs. at 25° C. After 3 washes with PBS/tween-20 (Bio-Rad), pH 7.5, plates were incubated with 3% BSA/PBS for 2 hrs. at 37° C., washed twice and a 100 μl of diluted serum was added in quadruplicate. The plates were incubated for 2 hrs. at 37° C. After three rinses with PBS/tween-20, plates were incubated with 100 μl/well of peroxidase-conjugated goat anti-rat IgG antibody (Tago, USA) diluted 1:1000 in 1% BSA/PBS for 1 hr. at 25° C. Color reaction was obtained by exposure to D-phenylenediamine (0.4 mg/ml phosphate citrate buffer, pH 5.0) containing 30% $H_2O_2$. The reaction was stopped by adding 0.4N $H_2SO_4$ and the OD 492 nm was read on an ELISA reader. The results shown in Table IX represents the percent suppression of the antigen proliferation of PLNC in the presence of SPC obtained from MBP fed rats compared to their responses to MBP in the presence of SPC obtained from intact rats. It is demonstrated that SPC obtained from MBP fed rats (group 1) suppresses the responses of PLNC to MBP (70%). Depletion of T cells (group 2) or suppressor/cytotoxic T lymphocytes (group 3) abrogates suppression. However, depletion of helper T lymphocytes (CD4, group 4) enhances the inhibition of the anti-MBP proliferation response of the PLNC. Diluting the CD4 depleted SPC results in decreasing of suppression from 96% (in the 1:1 ratio) to 18% (in the 1:100 ratio of SPC:PLNC).

These results suggest that the cells responsible for both disease inhibition and antigen-specific cellular responses in vitro are of the T cell origin and that they are suppressor/cytotoxic T lymphocytes.

TABLE IX

Suppression of anti-MBP responses of PLNC in the presence of irradiated SPC and its subpopulations, obtained from MBP fed rats.

| Group | SPC removed from MBP fed rats | SPC:PLNC ratio | % Suppression of PLNC responses to MBP |
|---|---|---|---|
| 1 | Whole population | 1:1 | 70 |
| 2 | CD3 depleted | 1:1 | −13 |
| 3 | CD8 depleted | 1:1 | −30 |
| 4 | CD4 depleted | 1:1 | 96 |
|   | "                | 1:10 | 32 |
|   | "                | 1:50 | 35 |
|   | "                | 1:100 | 18 |

Spleens were removed from MBP fed Lewis rats, then cells were harvested, irradiated and seeded along with responder PLNC removed from MBP/CFA immunized syngeneic rats. The SPC were used as untreated cells or depleted of CD3, CD4 or CD8 T lymphocytes using the appropriate monoclonal antibodies for coupling and then panning. Results are expressed as percent suppression of PLNC responses to MBP and are relative to the PLNC responses in the presence of irradiated SPC removed from unfed rats.

Example 14

Figures 6A, 6B:
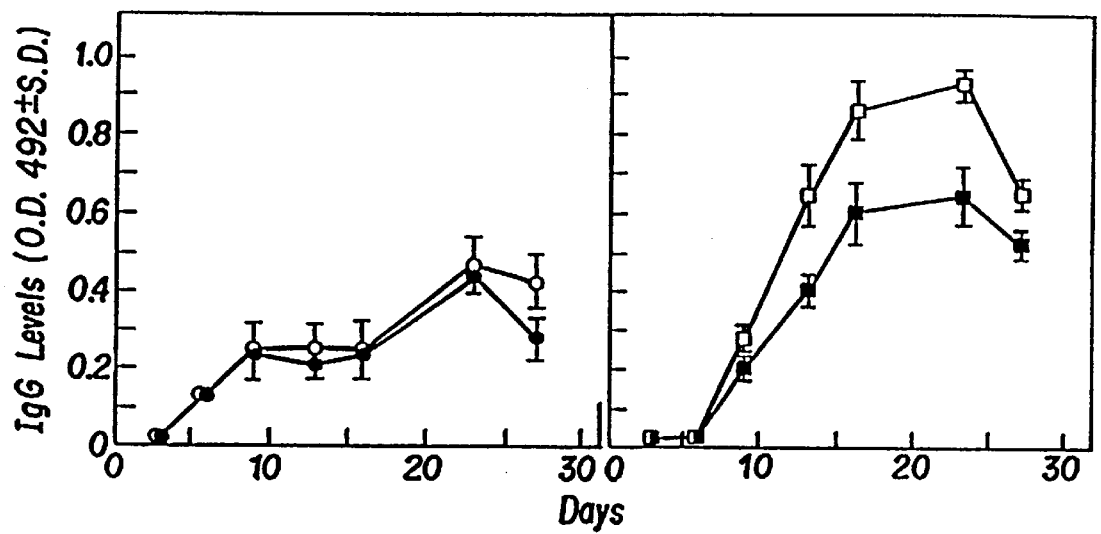
FIG. 6 is a graph which demonstrates the specific suppression of IgG responses to MBP after oral MBP feeding. Rats were bled at intervals and sera examined for anti-OVA (FIG. 6A, open circles) or anti-MBP (FIG. 6B, open squares) antibodies. These sera were compared to sera obtained from unfed and challenged animals (closed symbols). Results are expressed as ELISA O.D. 492 levels ±S.D.

Humoral Suppression of Anti-MBP IgG Production Induced by Oral Tolerance to MBP Lewis rats were either fed with MBP or left untreated and then challenged with MBP mixed with ovalbumin (OVA) emulsified in CFA. The rats were then bled at various intervals, and sera was examined for anti-OVA or anti-MBP antibodies. As shown in FIG. 6a, the IgG serum levels to OVA were not affected in MBP fed rats, whereas IgG serum levels to MBP were decreased in MBP fed rats (6b).

Example 15

Determination of the Cell Type Responsible for the Suppression of IgG Production In Vitro Lewis rats were fed with MBP or remained unfed and then were immunized with MBP+OVA/CFA. The PLN were removed 12 days later, and the PLNC were cultured for 3 days in the presence of either MBP or OVA, the supernatants were collected, diluted 1:20 and examined for their IgG contents. As shown in Table X, PLNC, which were obtained from fed rats (group 2) and cultured in vitro with MBP, responded less in terms of IgG production to MBP in comparison to PLNC obtained from unfed rats (group 1, 45% suppression). The production of anti-OVA IgG production in PLNC from the same rats was not affected, (group 4 vs. 5). Moreover, mixing irradiated PLNC obtained from MBP fed and immunized rats with PLNC of immunized rats cultured together with MBP, decreased the antibody production of the later (group 3, 35% suppression), whereas the antibodies titers against OVA was not affected (group 6). In addition, removal of CD8+ cells abrogated the suppression of anti-MBP antibodies demonstrating that, as in adoptive transfer and proliferative responses, CD8+ cells were responsible for suppression.

TABLE X

| | | | | IgG Levels in Supernatants | |
|---|---|---|---|---|---|
| Group | Responder Cells | Modulator Cells | In Vitro Stimulation | O.D. 492 Values ± S.D. | % Suppression of IgG Production |
| 1 | Immunized | — | MBP | 0.56 ± 0.06 | — |
| 2 | MBP Fed and Immunized | — | MBP | 0.31 ± 0.01 | 45 |

TABLE X-continued

| Group | Responder Cells | Modulator Cells | In Vitro Stimulation | O.D. 492 Values ± S.D. | % Suppression of IgG Production |
|---|---|---|---|---|---|
| 3 | Immunized | MBP Fed and Immunized | MBP | 0.36 ± 0.04 | 35 |
| 4 | Immunized | MBP Fed and Immunized CD8+ depleted | MBP | 0.55 ± 0.04 | 0 |
| 5 | Immunized | — | OVA | 0.17 ± 0.03 | — |
| 6 | MBP Fed and Immunized | — | OVA | 0.18 ± 0.02 | 0 |
| 7 | Immunized | MBP Fed and Immunized | OVA | 0.21 ± 0.04 | 0 |

Rats were immunized with MBP + OVA and CFA (some 3 days after the fifth feeding of MBP). Twelve days later their PLNC were removed and cultured together with MBP (groups 1–4) or with OVA (groups 5–7) for three days. In some groups, irradiated PLNC obtained from MBP fed and immunized rats were irradiated and cultured along with immmunized PLNC in the presence of MBP (group 3) or in the presence of OVA (group 7). The supernatants of these stimulations were collected, diluted and IgG levels determined by ELISA.

Example 16

Identification of the MBP Region which Actively Suppresses EAE using Overlapping Synthetic Polypeptides of MBP Overlapping fragments of the amino acid 1–37 fragment of guinea pig myelin basic protein were synthesized using solid phase peptide technique. Houghten, R., *Proc. Natl. Acad. Sci. USA* 82:5131–5135 (1985). These fragments were then administered orally in equimolar concentrations to 15 mg of whole myelin basic protein. They were administered on day −7, −5, and −2 prior to immunization. Animals were then challenged with basic protein in Freund's adjuvant according to established procedures and scored.

Animals were scored for mortality, presence of disease, and disease severity. As shown in Table XI, 6/6 control animals became ill with a mortality of 3/6. In animals receiving overlapping peptide fragments, there was decreased mortality using all fragments, except for fragment 1–10. When viewed in terms of disease severity, the region of the molecule between amino acids 5 and 20 shows the most pronounced diminution of disease. These results demonstrate that in the amino acid region 1–37 which itself is a suppressogenic fragment, specific regions of the molecule may be more or less suppressive when administered orally.

TABLE XI

| | EAE Mediated by MBP/CFA | | |
|---|---|---|---|
| Fragment | Incidence of Disease | Mean Max. Score | Mortality |
| Control (PBS) | 6/6 | 3.8 | 3/6 |
| 1–10 | 5/5 | 3.8 | 4/5 |
| 5–15 | 4/5 | 2.1 | 1/5 |
| 11–20 | 4/5 | 2.0 | 0/5 |
| 16–25 | 4/5 | 2.6 | 0/5 |

TABLE XI-continued

| | EAE Mediated by MBP/CFA | | |
|---|---|---|---|
| Fragment | Incidence of Disease | Mean Max. Score | Mortality |
| 21–30 | 5/5 | 3.0 | 1/5 |
| 26–36 | 4/6 | 2.6 | 1/6 |
| 31–37 | 5/6 | 3.3 | 0/6 |

Overlapping fragments of the 1–37 region of guinea pig myelin basic protein were synthesized using solid phase peptide technique. These fragments were then administered orally in equimolar concentrations to 15 mg of whole myelin basic protein. They were administered on day −7, −5, and −2 prior to immunization. Animals were then challenged with basic protein in Freund's adjuvant according to established procedures and scored.

Example 17

Demonstration that Oral Route of Administration of a Protein Antigen Determines to which Fragment there is an Immune Response Animals were given whole myelin basic protein, either immunized in the foot pad with Freund's adjuvant or administered orally. Seven to 10 days thereafter, spleen and lymph node cells were removed and restimulated in vitro with different fragments of the basic protein molecule.

As shown in Table XII, when myelin basic protein is administered peripherally in Freund's adjuvant, the primary response is to the 44–89 encephalitogenic region as measured by proliferation. However, as shown in Table XIII, when it is administered orally, the primary response is to fragment 1–37, the non-encephalitogenic suppressor determinant.

TABLE XII

Proliferation to MBP fragments in Lewis rats immunized with whole MBP.

| | Counts Per Minute | Stimulation Index |
|---|---|---|
| Background | 3,292 | — |
| Whole MBP | 10,142 | 3.1 |
| MBP fragment 1–37 | 3,360 | 1.0 |
| MBP fragment 44–89 | 10,054 | 3.0 |

Animals were immunized in hind foot pads with 50 μg MBP in CFA. Ten days later lymph nodes were removed and stimulated in vitro with 10 μg MBP or equimolar amounts of MBP fragments.

TABLE XIII

Proliferation to MBP fragments in Lewis rats fed whole MBP orally.

| Source of LNC | Whole MBP | 1–37 | 44–89 |
|---|---|---|---|
| SPC | 5.10 ± 1.6 | 5.05 ± 1.8 | 2.41 ± 0.9 |
| Mes. LNC | 8.61 ± 1.9 | 9.88 ± 1.5 | 3.53 ± 0.8 |
| Cervicals | 4.58 ± 1.3 | 6.42 ± 0.9 | 2.51 ± 0.6 |

Animals were fed 1 mg of whole MBP x3, then cells removed from various organs 15 days following feeding and proliferation measured. Results are expressed as the change in CPM × $10^{-3}$ as compared to cells cultured alone.

What is claimed is:

1. A method of treating multiple sclerosis comprising orally or enterally administering a composition comprising MBP to a human suffering from multiple sclerosis, in an amount effective to suppress autoimmune response associated with said multiple sclerosis, the suppression of said response comprising elicitation of suppressor T-cells specific to MBP.

2. The method of claim 1 wherein said treatment suppresses the symptoms of said multiple sclerosis.

3. The method of claim 1 wherein said composition is administered orally.

4. The method of claim I wherein said composition is administered enterally.

5. The method of claim 1 wherein said composition comprises tissue that is the target of attack in said autoimmune disease.

6. The method of claim 1 comprising administering said composition in a solid form.

7. The method of claim 1 comprising administering said composition in a semi-solid form.

8. The method of claim 1 wherein said composition further comprises a pharmaceutically acceptable carrier.

9. A method of treating multiple sclerosis comprising orally or enterally administering to a human suffering from multiple sclerosis an effective amount for treating multiple sclerosis of a composition comprising MBP, said treatment comprising in elicitation of suppressor T-cells.

10. The method of claim 9 wherein said composition comprises tissue that is the target of attack in said autoimmune disease.

11. The method of claim 9 comprising administering said composition in a solid form.

12. The method of claim 9 comprising administering said composition in a semi-solid form.

13. The method of claim 9 wherein said composition comprises a pharmaceutically acceptable carrier.

14. A method of treating multiple sclerosis comprising orally or enterally administering a composition comprising MBP to a human suffering from multiple sclerosis, in an amount effective to suppress autoimmune response associated with said multiple sclerosis.

15. The method of claim 14 wherein said composition comprises tissue that is the target of attack in said autoimmune disease.

16. The method of claim 14 comprising administering said composition in a solid form.

17. The method of claim 14 comprising administering said composition in a semi-solid form.

18. The method of claim 14 wherein said composition comprises a pharmaceutically acceptable carrier.

19. A method for treatment of a human suffering from multiple sclerosis comprising orally or enterally administering to said human a composition comprising MBP in an amount effective to treat said multiple sclerosis.

20. The method of claim 19 wherein said composition comprises tissue that is the target of attack in said autoimmune disease.

21. The method of claim 19 comprising administering said composition in a solid form.

22. The method of claim 19 comprising administering said composition in a semi-solid form.

23. The method of claim 19 wherein said composition comprises a pharmaceutically acceptable carrier.

24. A method of treating multiple sclerosis comprising orally or enterally administering a composition comprising a peptide fragment of MBP to a human suffering from multiple sclerosis, in an amount effective to suppress autoimmune response associated with said multiple sclerosis, wherein said peptide fragment is effective to suppress said response.

25. The method of claim 24 comprising administering said composition in a solid form.

26. The method of claim 24 comprising administering said composition in a semi-solid form.

27. The method of claim 24 wherein said peptide is synthesized.

28. The method of treating multiple sclerosis comprising orally or enterally administering a composition comprising an analog of MBP to a human suffering from multiple sclerosis, in an amount effective to suppress autoimmune response associated with said multiple sclerosis, wherein said analog is effective to suppress said autoimmune response.

29. The method of claim 28 comprising administering said composition in a semi-solid form.

30. The method of claim 28 comprising administering said composition in a solid form.

* * * * *